United States Patent
Cumming

(10) Patent No.: US 7,981,155 B2
(45) Date of Patent: Jul. 19, 2011

(54) HYDROLIC ACCOMMODATING INTRAOCULAR LENS

(75) Inventor: J. Stuart Cumming, Laguna Beach, CA (US)

(73) Assignee: C&C Vision International Limited, Dublin (IE)

( * ) Notice: Subject to any disclaimer, the term of this patent is extended or adjusted under 35 U.S.C. 154(b) by 1013 days.

(21) Appl. No.: 11/458,886

(22) Filed: Jul. 20, 2006

(65) Prior Publication Data

US 2007/0129801 A1  Jun. 7, 2007

Related U.S. Application Data

(63) Continuation-in-part of application No. 11/297,232, filed on Dec. 7, 2005, now abandoned.

(51) Int. Cl.
*A61F 2/16* (2006.01)

(52) U.S. Cl. .................... 623/6.13; 623/6.16; 623/6.37; 623/6.51

(58) Field of Classification Search ................. 623/6.13, 623/6.32, 6.34, 6.37, 6.44
See application file for complete search history.

(56) References Cited

U.S. PATENT DOCUMENTS

| | | |
|---|---|---|
| 4,174,543 A | 11/1979 | Kelman |
| 4,244,060 A | 1/1981 | Hoffer |
| 4,254,509 A | 3/1981 | Tennant |
| 4,254,510 A | 3/1981 | Tennant |
| 4,298,996 A | 11/1981 | Barnet |
| 4,304,012 A | 12/1981 | Richard |
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,629,462 A | 12/1986 | Feaster |
| 4,664,666 A | 5/1987 | Barrett |
| 4,673,406 A | 6/1987 | Schlegel |
| 4,704,123 A | 11/1987 | Smith |
| 4,718,904 A | 1/1988 | Thornton |
| 4,738,680 A | 4/1988 | Herman |
| 4,753,655 A | 6/1988 | Hecht |
| 4,759,761 A | 7/1988 | Portnoy |
| 4,778,463 A | 10/1988 | Hetland |
| 4,813,955 A | 3/1989 | Achatz et al. |
| 4,816,030 A | 3/1989 | Robinson |
| 4,840,627 A | 6/1989 | Blumenthal |

(Continued)

FOREIGN PATENT DOCUMENTS

EP    0208546 A    1/1987

(Continued)

OTHER PUBLICATIONS

Archimede Busacca, Ciliary Muscle Physiology Studied by Gonioscopy, Annals of Oculistics, vol. CLXXXVIII, Jan. 1955 (English Translation), 13 pages.

(Continued)

*Primary Examiner* — David H. Willse
(74) *Attorney, Agent, or Firm* — Orrick, Herrington & Sutcliffe LLP

(57) ABSTRACT

An accommodating intraocular lens comprising an optic made from solid silicone and liquid silicone. The optic has a central anterior area or membrane that can vary in radius and thus change power.

17 Claims, 5 Drawing Sheets

U.S. PATENT DOCUMENTS

| | | | |
|---|---|---|---|
| 4,842,601 A | 6/1989 | Smith |
| 4,880,427 A | 11/1989 | Anis |
| 4,892,543 A | 1/1990 | Turley |
| 4,932,966 A | 6/1990 | Christie et al. |
| 4,932,970 A | 6/1990 | Valdemar |
| 4,963,148 A | 10/1990 | Sulc et al. |
| 4,994,082 A | 2/1991 | Richards et al. |
| 5,047,051 A | 9/1991 | Cumming |
| 5,078,742 A | 1/1992 | Dahan |
| 5,141,507 A | 8/1992 | Parekh |
| 5,171,319 A | 12/1992 | Keates et al. |
| 5,171,320 A | 12/1992 | Nishi |
| 5,217,490 A | 6/1993 | Sayano et al. |
| 5,275,624 A | 1/1994 | Hara et al. |
| 5,376,115 A | 12/1994 | Jansen |
| 5,476,514 A | 12/1995 | Cumming |
| 5,496,366 A | 3/1996 | Cumming |
| 5,522,891 A | 6/1996 | Klaas |
| 5,578,078 A | 11/1996 | Nakajima et al. |
| 5,674,282 A | 10/1997 | Cumming |
| 6,051,024 A | 4/2000 | Cumming |
| 6,129,760 A | 10/2000 | Fedorov et al. |
| 6,193,750 B1 | 2/2001 | Cumming |
| 6,197,059 B1 | 3/2001 | Cumming |
| 6,387,126 B1 | 5/2002 | Cumming |
| 6,494,911 B2 | 12/2002 | Cumming |
| 6,540,353 B1 | 4/2003 | Dunn |
| 6,551,354 B1 | 4/2003 | Massoud et al. |
| 6,554,859 B1 | 4/2003 | Lang et al. |
| 6,558,419 B1 | 5/2003 | Pham et al. |
| 6,638,306 B2 | 10/2003 | Cumming |
| 6,767,363 B1 | 7/2004 | Bandhauer |
| 7,018,409 B2 | 3/2006 | Glick et al. |
| 7,150,760 B2 | 12/2006 | Zhang |
| 2001/0001836 A1 | 5/2001 | Cumming |
| 2002/0128710 A1 | 9/2002 | Eggleston |
| 2002/0188351 A1 | 12/2002 | Laguette |
| 2003/0060880 A1 | 3/2003 | Feingold |
| 2003/0065387 A1 | 4/2003 | Callahan et al. |
| 2003/0187505 A1 | 10/2003 | Liao |
| 2004/0002757 A1 | 1/2004 | Lai et al. |
| 2004/0082993 A1* | 4/2004 | Woods ............ 623/6.28 |
| 2005/0137703 A1 | 6/2005 | Chen |
| 2006/0116764 A1 | 6/2006 | Simpson |

FOREIGN PATENT DOCUMENTS

| | | |
|---|---|---|
| EP | 0336877 A1 | 10/1989 |
| EP | 0941717 A | 9/1999 |
| GB | 2171912 A | 9/1986 |
| WO | WO 95/06446 | 3/1995 |
| WO | WO 96/15734 A2 | 5/1996 |
| WO | WO 01/97742 A2 | 12/2001 |
| WO | WO 2004/046768 A2 | 6/2004 |
| WO | WO 96/25126 A1 | 8/2006 |
| WO | WO 2007/011879 A | 1/2007 |
| WO | WO 2007/037180 A | 4/2007 |

OTHER PUBLICATIONS

Archimede Busacca, La Physiologid Du Muscle Ciliarire Etudiee par la Gonioscopie, Armies D'Oculistique, vol. CLXXXVII, 1st Livraison, Janvier 1955 (French Translation), pp . 1-21.

D. Jackson Coleman, M.D., On The Hydraulic Suspension Theory Of Accommodation, Tr. Am. Opth. Soc. vol. LXXXIV, pp. 846-868, 1986.

J. Stuart Cumming, M.D., Accommodating Intra-Ocular Lens Development & Clinical Results, PowerPoint presentation 1999-2000, 14 pages.

Lee, Judith, "Update on IOLs," Outpatient Surgery (Mar. 2002), printed Oct. 26, 2004 (http://www.outpatientsurgery.net/2002/os03/f4.shtml) 5 pages.

Zhang, Z. et al., "A clinical study of posterior capsular opacification after implantation of foldable intraocular lenses with different edges of optics," Zhonghua Yan Ke Za Zhi 38(10):606-609 (Oct. 2002), printed Oct. 26, 2004 (http://www.ncbinlm.nih.gov/entrez/query.fcgi?cmd=Retrieve&db=pubmed&dopt=Abstract&list...).

Masket, Samuel, "Continuing Medical Education: Oct. 2003 IOL Edge Design, and PCO Dysphotopsia," Review of Ophthalmology, printed Oct. 26, 2004 (http://www.revophth.com/index.asp?ArticleType=SiteSpec&page=cme/oct03/lesson.htm), 10 pages.

Sabbagh, Leslie, "IOL Design Closes Off PCO," Review of Ophthalmology, printed Oct. 26, 2004 (http://www.revophth.com/index.asp?page=1_255.htm), 3 pages.

* cited by examiner

HYDROLIC ACCOMMODATING INTRAOCULAR LENS

This application is a continuation-in-part of application Ser. No. 11/297,232 filed Dec. 7, 2005, now abandoned, the disclosure of which is expressly incorporated herein by reference.

BACKGROUND

Intraocular lenses have for many years had a design of a single optic with loops attached to the optic to center the lens and fixate it in the empty capsular bag of the human lens. In the mid '80s plate lenses were introduced, which comprised a silicone lens, 10.5 mm in length, with a 6 mm optic. These lenses could be folded but did not fixate well in the capsular bag, but resided in pockets between the anterior and posterior capsules. The first foldable lenses were all made of silicone. In the mid 1990s an acrylic material was introduced as the optic of lenses. The acrylic lens comprised a biconvex optic with a straight edge into which were inserted loops to center the lens in the eye and fixate it within the capsular bag.

Recently accommodating intraocular lenses have been introduced to the market, which generally are modified plate haptic lenses and, like the silicone plate haptic lenses, have no clear demarcation between the junction of the plate with the optic's posterior surface. A plate haptic lens may be referred to as an intraocular lens having two or more plate haptics joined to the optic.

Flexible acrylic material has gained significant popularity among ophthalmic surgeons. In 2003 more than 50% of the intraocular lenses implanted had acrylic optics. Hydrogel lenses have also been introduced. Both the acrylic and hydrogel materials are incapable of multiple flexions without fracturing.

The advent of an accommodating lens which functions by moving along the axis of the eye by repeated flexions somewhat limited the materials from which the lens could be made. Silicone is the ideal material, since it is flexible and can be bent probably several million times without showing any damage. Additionally a groove or hinge can be placed across the plate adjacent to the optic as part of the lens design to facilitate movement of the optic relative to the outer ends of the haptics. On the other hand, acrylic material fractures if it is repeatedly flexed.

An example accommodating lens is a type as disclosed in U.S. Pat. No. 6,387,126 and others in the name of J. Stuart Cumming.

SUMMARY OF THE INVENTION

According to a preferred embodiment of this invention, an accommodating lens comprises a lens with a flexible solid and interior liquid optic, preferably with two or more extended portions from the solid optic which may be plate haptics capable of multiple flexions without breaking, preferably along with fixation and centration features at their distal ends. There may be a hinge or groove across the extended portions adjacent to the optic to facilitate the anterior and posterior movement of the optic relative to the outer ends of the extended portions. On the other hand, the optic may be rigidly attached to the haptics. Also, haptics can be omitted.

According to the present invention the optic is of a foldable, flexible silicone, acrylic or hydrogel material with an interior of liquid silicone, and the haptics are of a foldable material that will withstand multiple foldings without damage, e.g., silicone. Preferably, the end of the plate haptics have T-shaped fixation devices and the haptics are hinged to the optic.

The lens of the present invention is made of solid silicon with liquid silicone both of which have the same refractive index, and have a specific gravity the same as or very similar to that of the aqueous solution of the natural eye. The power of the lens, before implantation into the eye, can be changed by (1) changing the radius of a posterior portion of the optic, and/or (2) by changing the volume of the liquid silicone in the lens optic during the manufacturing process, or after implantation by injecting liquid silicone of the same or different refractive index into the cavity of the lens. During accommodation with contraction of the ciliary muscle and an increase in the vitreous cavity pressure the posterior surface of the solid silicone posterior portion of the lens is pushed forward since it is surrounded by a silicone membrane. This causes bulging of a thinner anterior membrane thereby increasing its curvature, thus decreasing the radius of the anterior surface of the lens, for near vision. The thin anterior membrane may be thicker in its periphery such that an increase in pressure inside the lens would product a central bulging of the membrane. This structure simulates the structure of the anterior capsule of the human lens and simulates its function. The posterior solid central. optic portion may have additional single or multiple spherical components or may be aspherical on one or both of its surfaces. Also, the increase in vitreous cavity pressure can tilt the lens to further facilitate accommodation.

Accordingly, features of the present invention are to provide an improved form of accommodating lens formed from solid and liquid silicone.

DESCRIPTION OF THE PREFERRED EMBODIMENT

Figure 1:
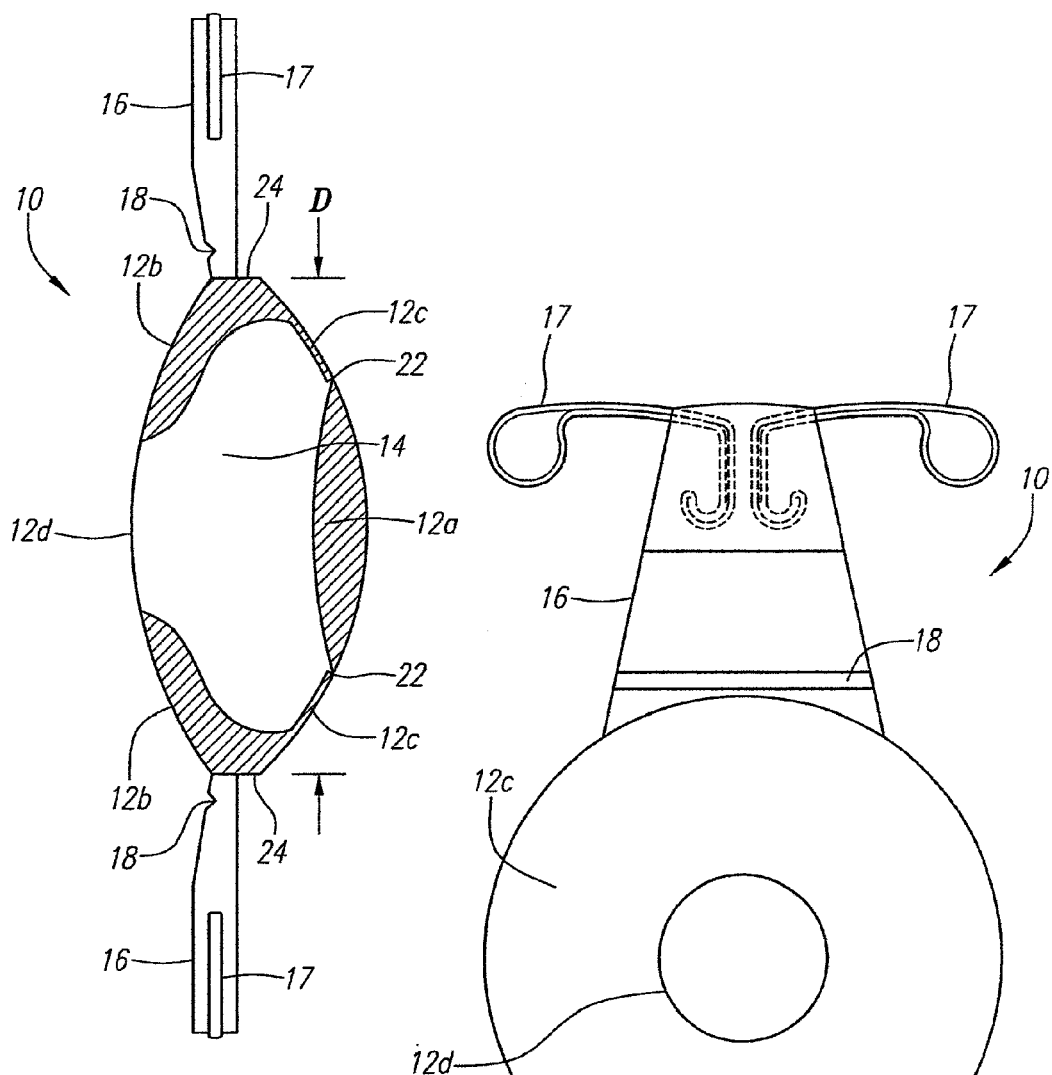
FIG. 1 is a side cross sectional view of the preferred embodiment of the lens of the present invention.
Figure 2:
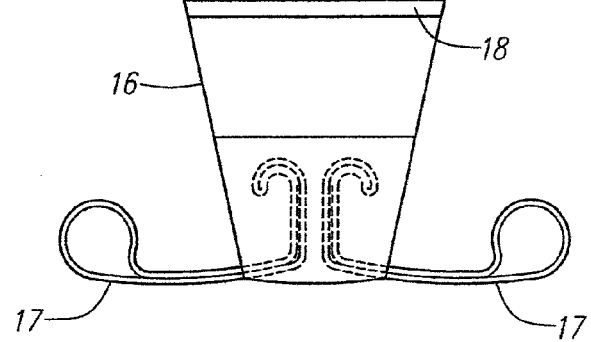
FIG. 2 is a plan view from the posterior side of the lens.
Figure 3:
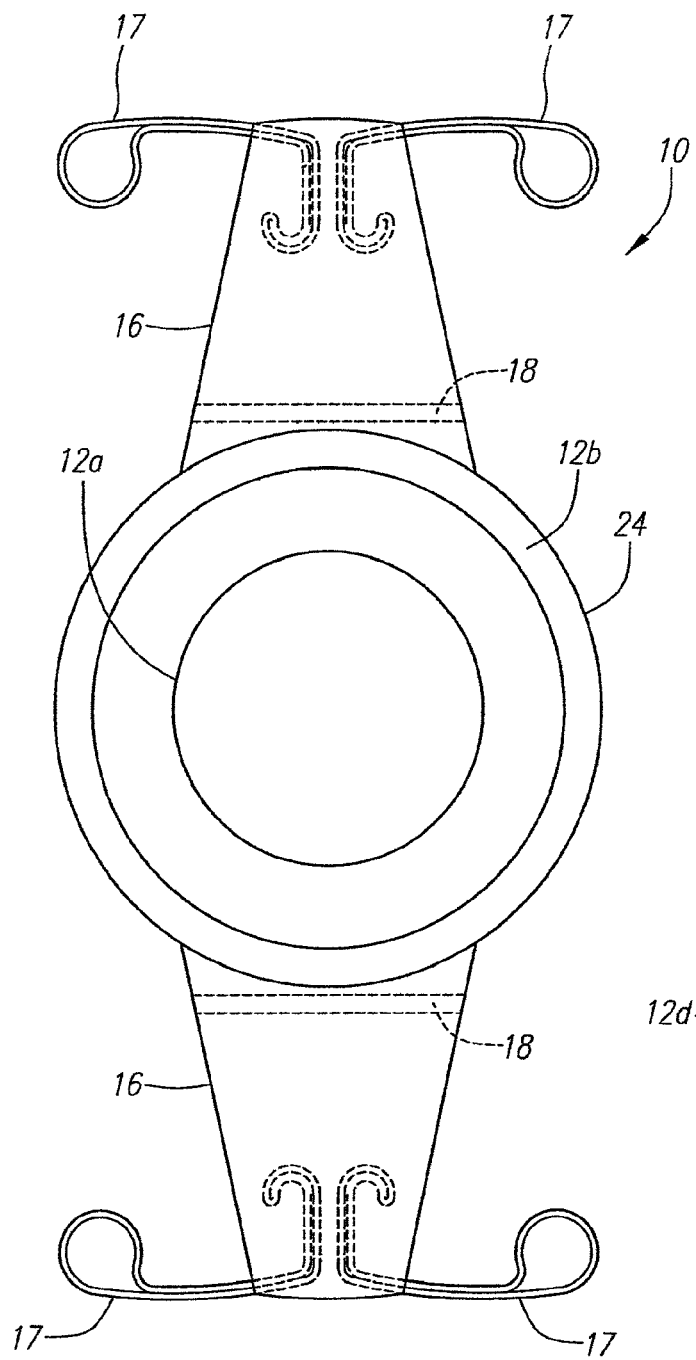
FIG. 3 is a plan view from the anterior side of the lens.

Turning now to the drawings, a preferred embodiment is shown in detail, comprising an intraocular lens with an optic 10 and haptics 16. The optic 10 is formed of two components, namely, a flexible solid portion 12 (12*a*-12*d*) preferably made of silicone, acrylic or hyrdrogel, and an interior liquid silicone portion 14. The portions 12*a* and 12*b* are sufficiently solid to prevent defomation of the optic 10 upon implantation into the fibrosed capsular bag of the eye. The flexible extending portions 16 may be plate haptics which are capable of multiple flexations without damage, and formed, for example, of silicone. The optic 10 and haptics 16 preferably are uniplanar, and two or more haptics 16 extend distally from opposite sides of the optic 10. The outer ends of the haptics 16 may include flexible fingers 17 such as disclosed in U.S. Pat. No. 6,387,126 to Cumming. Preferably the edge 24 of the optic is a 360° square edge.

Figure 4:
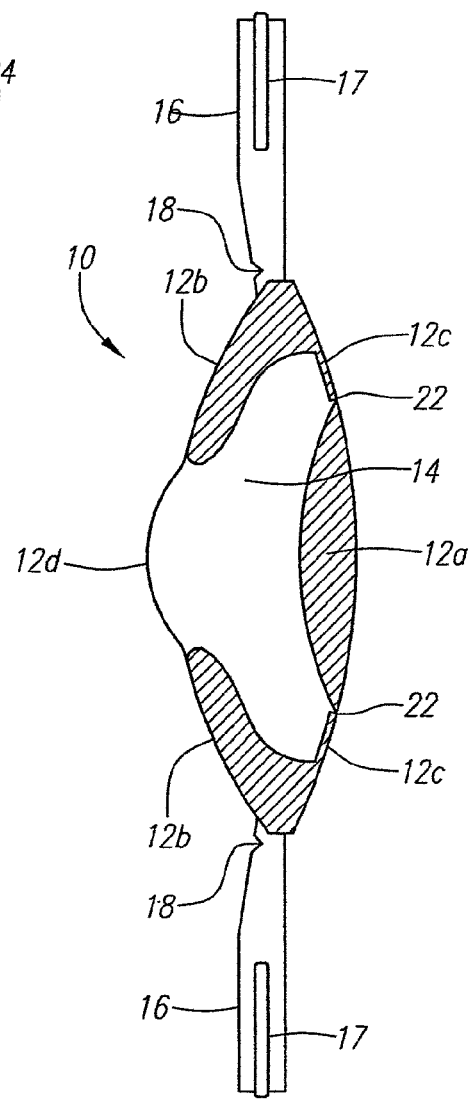
FIG. 4 is a cross-sectional view of the lens like FIG. 1 but showing bulging or increased curvature of an anterior portion of the lens.

The lens 10 includes portions 12*a*, 12*b* and 12*d* of solid silicone and wherein the portion 12*c* is substantially thinner, and 12*d* is even thinner than 12*c*, to enable a degree of flexibility as can be seen in comparing FIG. 1 and FIG. 4. The interior 14 is of liquid silicone. As is known, the specific gravity of the silicone used in this lens can be the same as or very similar to that of the acqueous solution in the human eye. This results in either no or negligible defomation of the liquid portion of the lens by gravity. The liquid silicone 14 has the same or similar refractive index as the solid components 12. The solid posterior radius of portion 12a prevents defomation of the posterior refracting surface. The radius of the portions 12a or 12b can be changed, during manufacturing, to select the desired power for the lens. Also, the power can be changed, during manufacturing, by changing the volume of the liquid silicone 14 in the lens optic 10.

In accommodating, the posterior surface portion 12a is pushed forward (to the left in FIGS. 1 and 4) by vitreous cavity pressure with constriction of the ciliary muscle. The anterior portion 12d bulges with increased curvature, that is decreased radius, of the anterior portion 12d such as illustrated in FIG. 4.

Example dimensions are 4.5-10.5 mm in overall diameter of portion 12b from D to D in FIG. 1, up to a 5 mm diameter portion 12d, and a 3-6 mm thickness (from right to left) in FIG. 1. A typical thickness for the solid silicon portions 12a and 12b is between 0.5 mm and 1.5 mm. The thickness of the anterior membrane 12d is very thin, preferably about that of a toy balloon, and the thickness of the annulus 12c is approximately two times that thickness to give sufficient flexibility to the solid posterior lens. The thickness at the hinge 18 area can be 0.1 mm. The hinge area 18 can be a "V" shape as shown but can be a square groove. Also, hinges 22 preferably are provided between 12c and 12a to facilitate anterior movement of the posterior optic 12a.

Furthermore, the power of the present lens can be changed after implantation in the eye by either injecting or removing liquid silicone from the optic 10.

The diameter of the portion 12d as well as its area can be less or more than that of the posterior portion 12a, dependent on the refractive range desired in the design of the lens.

Figure 5:
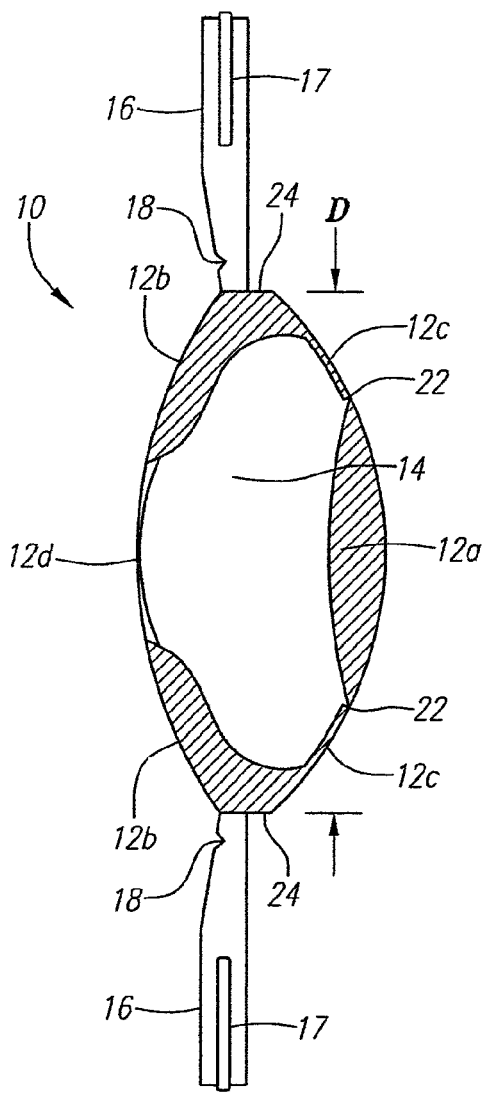
FIGS. 5 and 6 show variations in cross section.
Figure 6:
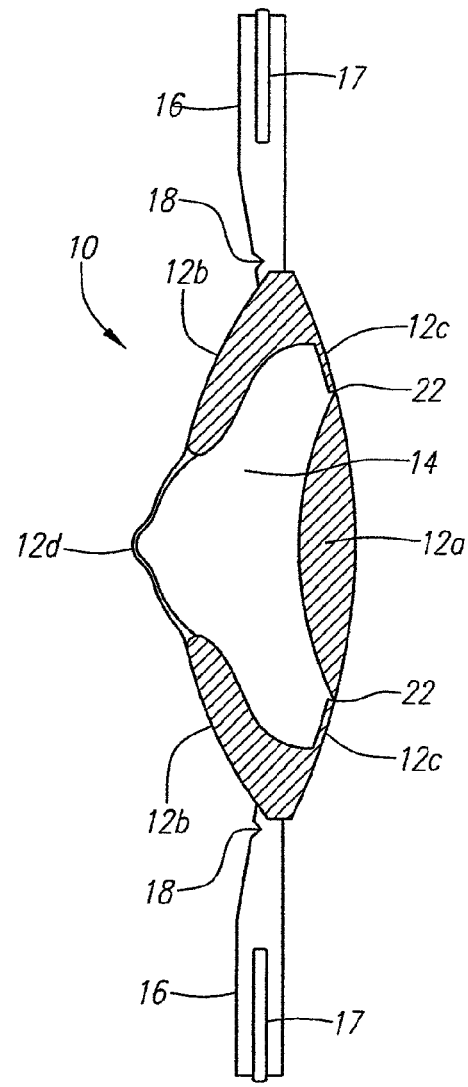
Figure 7:
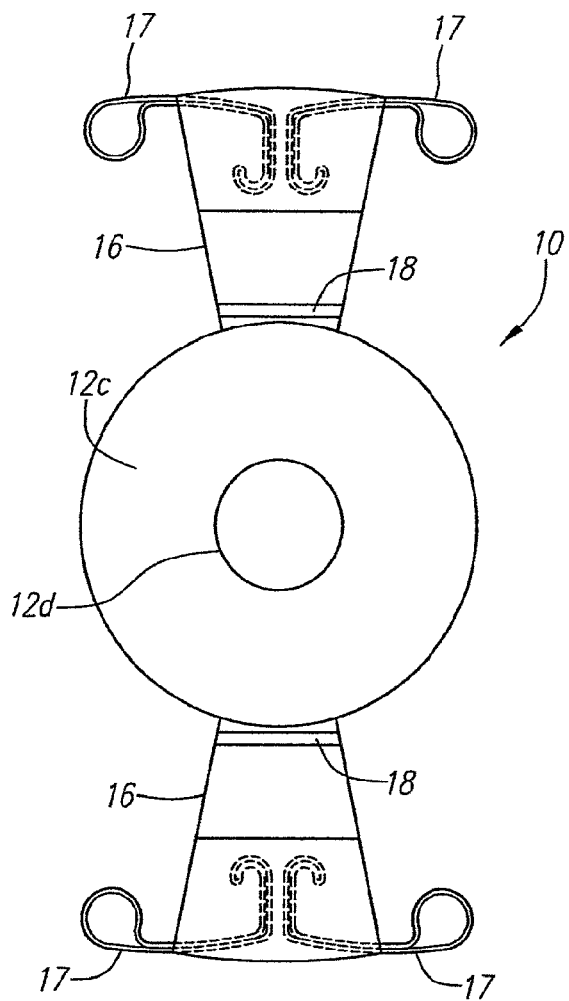
FIGS. 7-10 illustrate the lenses of the present invention with different forms of haptics.
Figure 8:
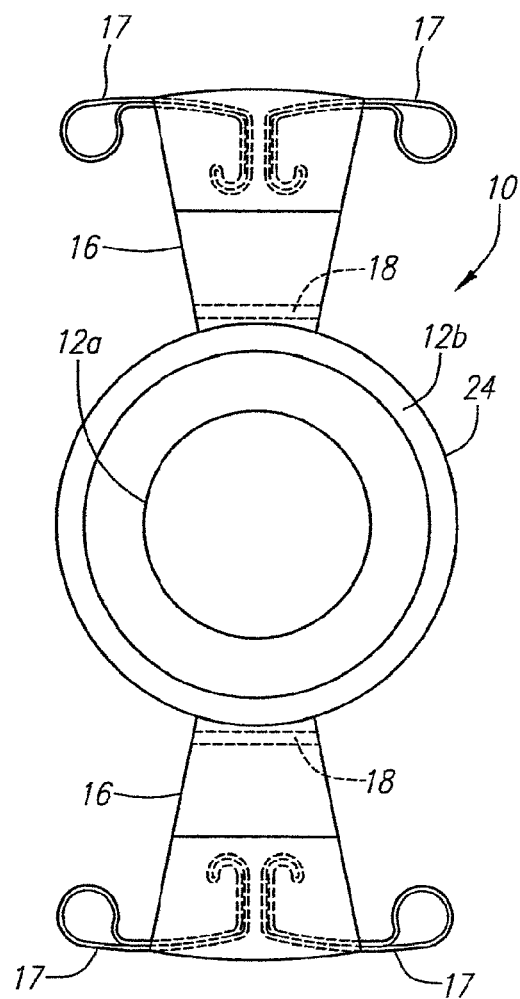
Figure 9:
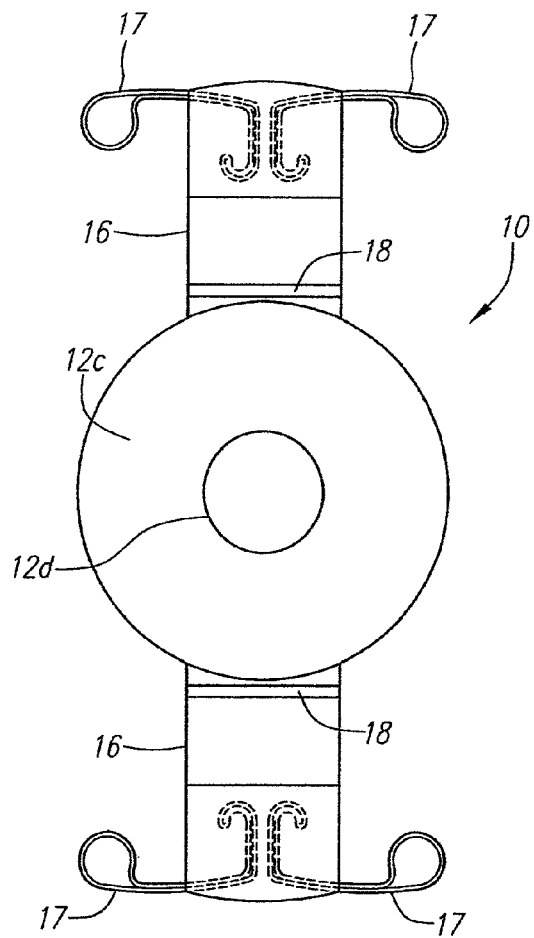
Figure 10:
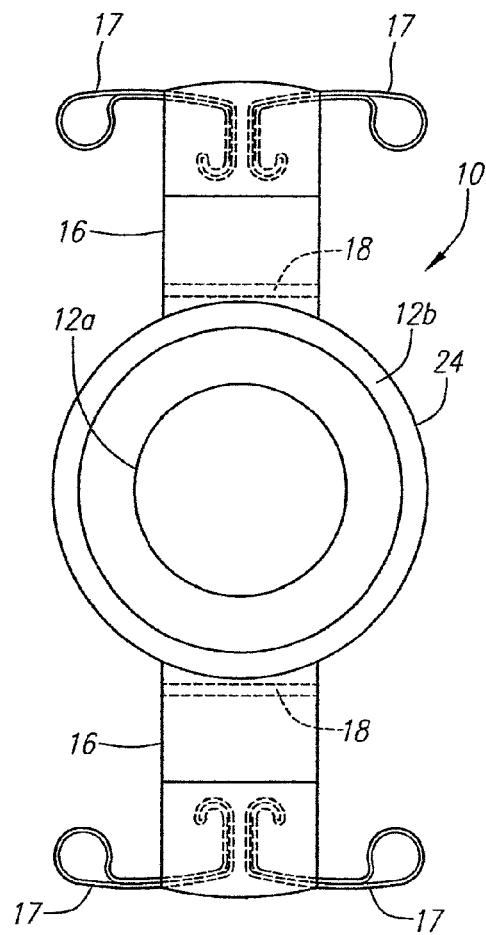

Turning now to the FIGS. 5-6 embodiment, it will be noted that anterior portion 12d is thinner in the middle, which will bulge more as shown in FIG. 6 under increased vitreous pressure.

As is well known in the art, an intraocular lens is implanted in the capsular bag of the eye after removal of the natural lens. The lens is inserted into the capsular bag by a generally circular opening cut in the anterior capsular bag of the human lens and through a small opening in the cornea or sclera. The outer ends of the haptics, or loops, are positioned in the cul-de-sac of the capsular bag. The outer ends of the haptics, or the loops, are in close proximity with the bag cul-de-sac, and in the case of any form of loops, the loops are deflected. Knobs can be provided on the outer end portions of the loops for improved securement in the capsular bag or cul-de-sac by engagement with fibrosis, which develops in the capsular bag following the surgical removal of the central portion of the anterior capsular bag.

As noted above, the haptics 16 may have a space or thin area 18 forming a hinge across their surface adjacent to the optic. This facilitates movement of the optic anteriorly and posteriorly relative to the outer ends of the haptics.

Accordingly, there has been shown and described a lens that comprises an optic of solid and liquid silicone and haptic loops or plates, preferably with fixation and/or centration protuberances at the ends of each haptic.

Various changes, modifications, variations, and other uses and applications of the subject invention will become apparent to those skilled in the art after considering this specification together with the accompanying drawings and claims. All such changes, modifications, variations, and other uses of the applications which do not depart from the spirit and scope of the invention are intended to be covered by the claims which follow.

What is claimed is:

1. An accommodating intraocular lens having an optic formed of solid silicone and liquid silicone,
   the optic being circular and having a posterior central portion of solid silicone extending by an annular membrane to a peripheral annular portion of thicker solid silicone than the annular membrane forming an outer diameter portion extending from a posterior side to an anterior side of the periphery of the optic, the optic further comprising a central anterior second portion extending to the anterior side of the annular solid portion, and comprising a single membrane which is substantially thinner than the posterior annular membrane, and capable of deformation, and a liquid silicone within the optic retained therein by the aforesaid solid portions and membranes, the optic being designed so that the thinner anterior membrane portion can change in radius of curvature upon an increase and decrease in the vitreous cavity pressure on the posterior central solid portion, and
   haptics extending from opposite sides of the lens, and loops on the outer ends of the haptics to help center and fixate the lens in the capsular bag of the eye.

2. The lens as in claim 1 whereby the optic can move anteriorly and posteriorly relative to outer ends of the haptics.

3. The lens as in claim 1 wherein the solid silicone and the liquid silicone have approximately the same specific gravity as the aqueous solution of a human eye.

4. The lens as in claim 1 designed such that compression of the posterior surface by vitreous pressure can cause a symmetrical bulging of an anterior surface of the anterior portion.

5. The lens as in claim 1 wherein the solid and liquid portions of the optic have substantially the same index of refraction.

6. The lens as in claim 1 wherein the optic has radii of curvature to give a patient within whom the lens is implanted emmetropia upon relaxation of the ciliary muscle.

7. The lens as in claim 1 having a radius of curvature of the back or front solid surface of the posterior or anterior portions can be changed, during manufacturing, to provide emmetropia for a designated eye.

8. The lens as in claim 1 wherein the power of the optic can be changed after implantation by changing the amount of liquid silicone in the optic.

9. The lens as in claim 1 wherein the thin anterior portion has a smaller area than the central posterior portion.

10. The lens as in claim 1 wherein the thin anterior portion has a larger area than the central posterior portion.

11. The lens as in claim 1 wherein the thin anterior thinner portion has a smaller diameter than the central posterior portion.

12. A lens as in claim 1 wherein the haptics have a hinge adjacent to the optic.

13. A lens as in claim 1 where there is a 360 degree square edge on the posterior side of the peripheral annular portion.

14. A lens as in claim 1 wherein the posterior central portion has a fixed central radius.

15. A lens as in claim 1 wherein an increase in vitreous cavity pressure can cause the lens optic to tilt to facilitate accommodation.

16. A lens as in claim 1 wherein the posterior membrane extends between a posterior axial portion and posterior and anterior outer portions of the optic, and the anterior membrane is centered on the anterior side of the lens.

17. An accommodating intraocular lens in which the optic comprises:
- an integral central optical system supported by a solid fixed radius, flexible annular peripheral optical component,
- a central anterior optical component comprising a thin deformable membrane,
- a central liquid optical material within the lens,
- a posterior central solid flexible optic surrounded by an annular membrane which is thicker and less resilient than the thin anterior membrane,
- the posterior optic being designed to move anteriorly and compress the liquid central optical material to cause the thin anterior membrane to bulge forward to decrease its radius of curvature and increase its refractive power upon an increase of vitreous cavity pressure upon ciliary muscle contraction, and
- haptics to support the optical system within the eye, the haptics extend from opposite sides of the lens and have loops on the outer ends of the haptics to help center and fixate the lens in the capsular bag of the eye.

* * * * *